United States Patent [19]

Greenspan

[11] 4,014,746

[45] * Mar. 29, 1977

[54] METHOD OF AND APPARATUS FOR COLLECTING CULTURES

[75] Inventor: Donald J. Greenspan, Riverside, N.J.

[73] Assignee: U.S. Medical Research and Development, Inc., Riverside, N.J.

[ * ] Notice: The portion of the term of this patent subsequent to June 24, 1992, has been disclaimed.

[22] Filed: June 23, 1975

[21] Appl. No.: 589,521

Related U.S. Application Data

[63] Continuation-in-part of Ser. No. 358,350, May 8, 1973, Pat. No. 3,890,954.

[52] U.S. Cl. .................. 195/103.5 R; 128/2 F; 128/2 W; 195/139; 128/269

[51] Int. Cl.² .................................... C12K 1/00

[58] Field of Search ............... 128/2 W, 2 F, 269; 195/139

[56] References Cited

UNITED STATES PATENTS

| | | | |
|---|---|---|---|
| 3,163,160 | 12/1964 | Cohen | 128/2 W |
| 3,388,043 | 6/1968 | Ingnorsen | 195/139 |
| 3,450,129 | 6/1969 | Avery et al. | 128/2 W |
| 3,508,653 | 4/1970 | Coleman | 128/2 F |
| 3,579,303 | 5/1971 | Pickering | 195/103.5 R |
| 3,776,220 | 12/1973 | Monaghan | 128/2 W |
| 3,890,954 | 6/1975 | Greenspan | 195/139 |

*Primary Examiner*—A. Louis Monacell
*Assistant Examiner*—Robert J. Warden
*Attorney, Agent, or Firm*—Woodcock Washburn Kurtz & Mackiewicz

[57] ABSTRACT

A swab is packaged in a tube having an open end and containing a culture-sustaining liquid at the bottom of a tube, and a plug including a one-way isolating valve located above the liquid and a barrier member forming an air-tight chamber between the plug and the barrier member. After removal of the swab from the tube and swabbing of a body canal or the like with the absorbent tip of the swab, the swab may be placed back in the tube with the absorbent tip adjacent the plug and within the substantially air-tight chamber. The plug may then be forced downwardly through the liquid by pressing on the end of the swab or another rigid member telescoped within the tube so as to force the liquid up through the valve into contact with the absorbent tip. A closure or cap which may be used to press on the end of the stick or the rigid member then forms a seal at the open end of the tube.

22 Claims, 11 Drawing Figures

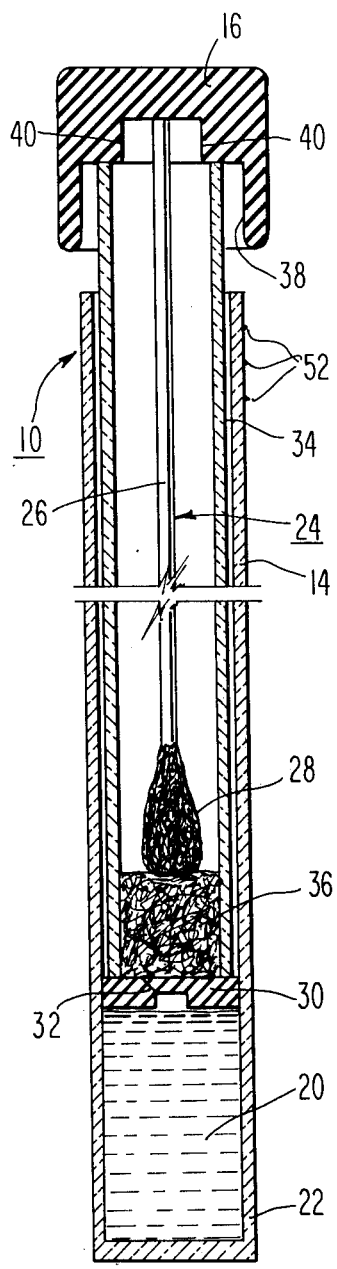
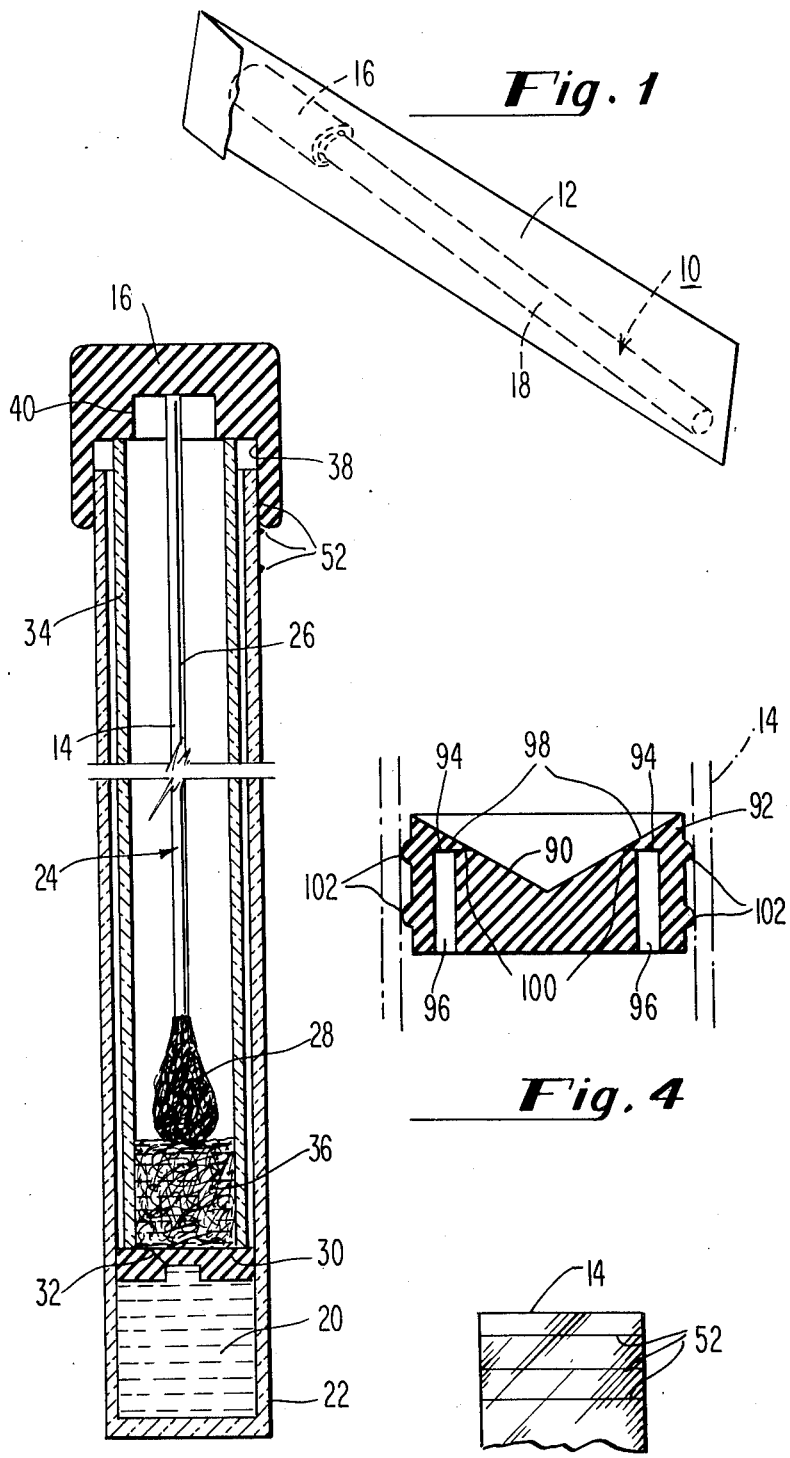
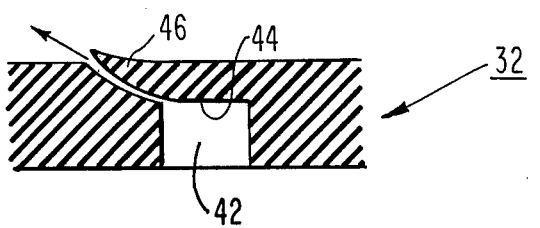

METHOD OF AND APPARATUS FOR COLLECTING CULTURES

RELATED CASES

This is a continuation-in-part of application Ser. No. 358,350 filed May 8, 1973 which will issued on June 24, 1975 as U.S. Pat. No. 3,890,954.

BACKGROUND OF THE INVENTION

This invention relates to a swabbing method and apparatus for use by physicians and technicians for collecting a culture as from various areas of a patient's body, such as the ears, the nose and throat, and for keeping a culture moist and alive for a period of time after it is collected.

In general, this is accomplished through the use of a container which receives the culture-carrying swab and bathes the swab in a culture-sustaining liquid. U.S. Pat. No. 3,450,129—Avery et al. discloses a particular container unit for this purpose. The container carries its own supply of liquid in a frangible ampoule along with a swab, all of which is packaged in a sanitary wrapper. After the swab has been removed from the wrapper and container and a culture has been taken, the swab is inserted back into the container, a cap is applied to the end of the container and the frangible ampoule is broken so as to bathe the absorbent tip of the swab in the culture-sustaining liquid which was encapsulated in the ampoule.

Another container is disclosed in the U.S. Pat. No. 3,776,220—Monaghan. The container also carries its own sealed supply of liquid below a first sealed area in the tube and the swab itself, prior to use, in located in the tube such that the absorbent tip is positioned immediately above the sealed area and below a restricted area. After the culture is taken, the swab is reinserted into the container, through the restricted area and the sealed area so as to reach the culture-sustaining liquid at the bottom of the tube. The sealed area immediately above the culture-sustaining liquid no longer forms a seal but permits air to enter the area of the absorbent tip and the culture-sustaining liquid.

Another container is disclosed in the U.S. Pat. No. 3,163,160—Cohen which utilizes a member including a valve initially positioned above the culture-sustaining liquid. After the culture has been taken, the bottom of the container may be squeezed so as to force the culture-sustaining liquid upwardly through the valve into saturating contact with the absorbent tip of the swab. There is no movement of the valve member in response to movement of the swab or the absorbent tip. In fact, the absorbent tip of the swab does not contact the valve member.

U.S. Pat. No. 3,579,303—Pickering discloses a flexible swab container in combination with a clip which may be utilized to form a seal between the flexible container and the elongated member which extends to the absorbent tip of the swab which is submersed in a culture-sustaining liquid. Still another sampling unit is disclosed in U.S. Pat. No. 3,388,043—Ingvorsen.

German Pat. No. 285,835 discloses a container including a valve member for use in moistening a swab with a disinfecting liquid. However, the swab itself is not used to force the plug through the disinfecting liquid. Rather, a plunger connected to the plug from the other side of the swab moves the plug through a tube.

U.S. Pat. No. 3,508,653—Coleman discloses a plug having a valve for serum separation. It does not however suggest that such a valve could be utilized in combination with a swab stick to control the introduction of a culture-sustaining liquid into contact with the absorbent tip of the swab.

SUMMARY OF THE INVENTION

It is an object of this invention to provide a swab containing unit which is capable of use with an aerobic or anaerobic culture.

It is a more specific object of this invention to provide a swab containing unit which is capable of moistening the absorbent tip of a swab in a substantially air-tight chamber substantially filled with a culture-sustaining liquid so as to permit the use of the container with anaerobic cultures.

In accordance with these and other objects of the invention, apparatus is provided for collecting cultures and the like comprising a hollow tubular container having a closed end, an open end and sides extending therebetween. A culture-sustaining liquid is positioned within the tubular container adjacent the closed end. A barrier member extends across the tubular member so as to form a substantially leak-proof barrier between the closed end and the open end. When a swab including an elongated member and an enlarged absorbent tip is inserted into the container such that the absorbent tip passes through an opening in the barrier member, a seal is formed around the elongated member. Thus a substantially air-tight chamber is formed beneath the barrier member so as to permit the use of the apparatus in collecting anaerobic cultures where a suitable culture-sustaining liquid such as Stuart's Modified Media manufactured by Difco Laboratories.

In a particularly preferred embodiment of the invention, the barrier member comprises an elastic material so as to permit the opening to enlarge as the absorbent tip passes therethrough and to contract in sealing engagement with the elongated member after the absorbent tip passes therethrough. In this connection, the barrier member may comprise a greater thickness near the sides of the tubular container than near the opening. In addition, the surface of the barrier adjacent the open end of the tubular member may taper inwardly and toward the closed end so as to guide the absorbent tip toward the opening.

In accordance with another important aspect of the invention, the apparatus further comprises a movable piston member extending across the tubular member and in sealing engagement with both sides thereof between the closed end and the barrier member. The piston member is movable through the culture-sustaining liquid toward the closed end when the swab is inserted through the opening in the barrier member and in pushing contact with the piston member. The piston member includes a one-way valve means for allowing the culture-sustaining liquid to enter the area between the barrier and the piston member when the swab is in pushing contact with the piston member.

The barrier member may be attached to the piston member so as to move together through the tubular member when the swab is in pushing contact with the piston member. In the alternative, the barrier member may be detached from the piston member so as to permit the piston member to move to the tubular member independently of movement of the barrier member.

BRIEF DESCRIPTION OF THE DRAWINGS

FIG. 1 is a perspective view of a swabbing apparatus embodying the invention in its wrapper;

FIG. 2 is a sectional view of the swabbing apparatus embodying the invention;

FIG. 2a is an enlarged view of a valve in the plug of the swabbing apparatus shown in FIG. 2;

FIG. 2b is a partial elevational view of the markings on the container tube shown in FIG. 2;

FIG. 3 is a sectional view of the swabbing apparatus of FIG. 2 after the culture-carrying swab has been sealed into its container tube;

FIG. 4 is a sectional view of a piston member or plug which may be utilized in the apparatus of FIGS. 2 and 3;

DETAILED DESCRIPTION OF PREFERRED EMBODIMENTS

Figure 5:
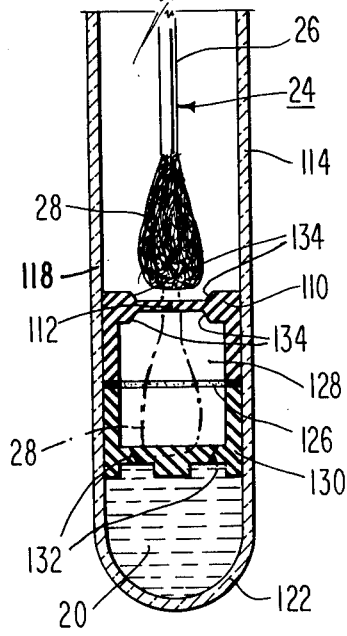
FIG. 5 is a sectional view of a swabbing apparatus representing another embodiment of the invention.

A swabbing apparatus 10 constructed in accordance with this invention for use in obtaining cultures is enclosed within a wrapper 12 comprising paper or the like as shown in FIG. 1. As shown in FIG. 2, the apparatus 10, which has been removed from the wrapper 12 of FIG. 1, comprises a container tube 14 and a closure member or cap 16 which is not sealed to the upper and open end 18 of the tube 14. The tube 14 contains a culture-sustaining liquid 20 at the closed end or bottom 22 of the tube 14 and remains isolated from a swab 24 comprising an elongated member or stick 26 and an absorbent tip 28. This isolation is achieved by a piston-like plug 30 comprising a substantially resilient material such as rubber or a plastic so as to resiliently and sealingly engage the walls of the tube 14. The plug 30 includes a one-way valve 32 which allows the liquid 20 to flow through an opening in the plug 30 when the plug is forced downwardly into the liquid 20 but maintains substantial physical isolation between the absorbent tip 28 of the swab 24 and a culture-sustaining liquid when the plug 30 is in the position shown in FIG. 2.

The tube 14 also contains an inner tube 34 on which the cap 16 (the cap is shown as shortened in length because of space limitations of the drawings) is resting which forms a chamber spaced and isolated from the sides of the tube and within which the swab 24 is located. An absorbent material 36 such as cotton, rayon or a foam is located within the chamber formed tube 34 supporting the tip 28 above the plug 30.

Once the apparatus 10 has been removed from the wrapper 12 as shown in FIG. 2, the cap 16 may be removed from the upper end of the inner tube 34. A swab 24 may then be grasped between the finer tips at the upper end protruding from the inner tube 34 and removed from the tube 14. At that time, the absorbent tip 28 may be brought into contact with that portion of the body from which a culture is to be taken and reinserted back into the inner tube 34.

At this time, the plug 30 is pushed downwards through the liquid 20 by pressing on the cap 16 which in turn presses on the upper end of the inner tube 34 so as to transmit the downward force therethrough to the plug 30 moving it to the position shown in FIG. 3. Note that the level of the liquid 20 now extends above the bottom of the inner tube 34 so as to saturate the absorbent material 36 and thereby assure that the tip 28 remains moist to keep the culture alive.

In order for the cap 16 to perform this pushing function with respect to the plug 30, the inside of the cap has a particular configuration. An elongated sealing surface 38 is provided which is adapted to engage the outside of the container tube 14 so as to isolate, at least to some degree, the contents of the tube once the surface 38 has been brought into contact with the outside of the tube 14. In addition, the cap 16 includes a shoulder which extends substantially perpendicular to the axis of the cap 16 so as to provide a surface which pushes against the upper end of the tube 34. Finally, the cap 16 includes a recess 40 which receives the upper end of the swab stick 26. The recess 40 has slightly less depth that the protrusion of the swab stick 26 beyond the end of the tube 34 to assure the swab 24 is, to some degree, forced into the cotton 36.

The nature of the one-way isolating valve in the plug 30 is shown in some detail in the enlarged view of FIG. 2a. The valve 32 includes a hole 42 which extends upwardly from the underside of the plug 30. An inclined slit is provided which extends from the upper surface of the plug 30 at one side of the hole 42 down to the upper end of the hole 42 so as to form a flap 46 which is biased to the closed position when the plug 30 is stationary within the liquid 20 and pressure on the opposite side of the plug 30 are substantially equal. It will be understood that the bias provided by the resilient material of the plug is sufficient to maintain the resilient flap 46 closed even when there is some pressure differential between opposite sides of the plug to be sure that the valve remains closed even when the tube 14 is inverted. For other details relating to the nature of this valve, reference is made to the inventor's own U.S. Pat. No. 3,661,265.

In accordance with another important aspect of the invention, a culture-sustaining liquid may be periodically introduced into the area above the plug 30 so as to extend the period in which the culture may be kept alive. For this purpose marks 52 shown in FIGS. 2 and 2b are provided on the exterior and upper end of the tube 14. When the cap is first placed on the tube 14 after the culture has been taken, it is pushed down to the first of the marks 52. It may then be sequentially advanced to the other marks at desirable intervals, e.g., every 24 hours, to keep reintroducing the liquid into contact with the absorbent material 36 and the absorbent tip 28 of the swab 24.

FIG. 4 discloses another plug or piston member 92 which may be substituted for the plug 30 of FIGS. 2 and 3. The plug 92 includes a downwardly and inwardly tapering surface 90 which, when utilized in conjunction with a similarly tapered cap which will be described with reference to FIG. 5, will serve to center the freely movable swab 24 along the axis of the tube thereby assuring the central, axially directed force on the plug 92. In addition to centering the tip 28 of the swab 24 on the plug 92, the tapered surface 90 also allows the swab 24 to assist in opening spaced one-way valve 94 which are located near the periphery of the plug 92. The valves 94 include elongated holes 96 extending substantially parallel with the axis of the plug and terminated by flaps 98 which are formed in part by the tapered surface 90. By observation it will be seen that any pressure located in the central area of the surface 90 will tend to collapse areas 100 of the plug beneath the flaps 98 so as to assist in opening the valves 94. It will also be seen that at least one valve 94 will be clear of the tip 28 to permit it to open.

Another embodiment of the invention is shown in FIG. 5 wherein a barrier member 110 extends across the tube 114 so as to form a substantially leak-proof barrier between a closed end or bottom 122 of the tube 114 and an open end so as to form a chamber 128 for the tip 28 of the swab 24. A plug member 130 includes a pair of valves 132 similar to the valves 32 as shown in FIG. 2a. The barrier member 110 and the plug 130 may be attached to one another by a suitable adhesive 126 or other means of affixing the barrier 110 in the plug 130.

After the absorbent tip 28 is inserted through the opening 112 and a seal is formed around the elongated member 26 of the swab 24, the swab 24 may be pushed downwardly so as to force the barrier member 110 and the plug member 130 downwardly through the culture-sustaining liquid 20 located at the bottom or closed end 122 of the tube. As the plug member 130 and the barrier member 110 advance toward the closed end 122, the culture-sustaining liquid moves upwardly through the valves 132 into the chamber 128. By moving the plug 130 sufficiently far through the culture-sustaining liquid 20, the chamber 128 may be substantially filled so as to eliminate or at least substantially eliminate all oxygen within the chamber 128.

In accordance with one important aspect of the invention, the barrier member 110 comprises suitable elastic material such as Kraton, supplied by Shell Chemical or TPR, supplied by Uniroyal, which will permit the opening 112 to enlarge thereby allowing the absorbent tip 28 of the swab 24 to pass therethrough while at the same time permitting the barrier member 110 to achieve sealing engagement with the elongated member 26 after the absorbent tip enters the chamber 128.

In accordance with another important aspect of the invention, the barrier member 110 comprises a greater thickness near the sides of the tube 118 than near the opening 112. This sectional configuration of the barrier member 110 permits sufficient flexibility of the barrier member at the opening 112 to allow insertion of the absorbent tip 28 while at the same time permitting the barrier member 110 to snap back into a sealing position around the elongated member 26 of the swab 24. As shown in FIG. 5, it may also be desirable to provide tapering portions 134 which lead from the area of greater thickness to the area of lesser thickness adjacent the opening 112.

As shown in FIg. 5, chamber 128 becomes substantially air-tight after the absorbent tip 24 has been inserted therein. Accordingly, it is possible to utilize the culture-collecting apparatus of FIG. 5 for anaerobic cultures by the proper choice of the culture-sustaining liquid medium 20. An anaerobic liquid medium which has been found to be particularly appropriate is Stuart's Modified Media manufactured by Difco Laboratories.

In accordance with another important aspect of the embodiment shown in FIG. 5, a cap 54 is provided with a skirt including an internal sealing surface 56 engaging the outside walls of the tube 114 and a recess comprising upwardly and inwardly tapered walls 58 leading to a flat surface 60 near the top of the cap 54. The purpose of the taper 58 is to provide a surface which will center the upper end of the elongated member or stick 26 with respect to the cap 54 and thereby direct the forces applied to the cap substantially axially downwardly through the tube 14 to move the plug 130 through the liquid 20 as shown in FIG. 5. Without the taper 58, the elongated member 26 may be off-center with respect to the cap 54 and this would apply a non-axial force to the plug 130 with the possibility of skewing it within the tube 114. Although this skewing would still permit the liquid to saturate the absorbent material of the tip 28, it would not permit the controlled periodic introduction of the liquid into contact with the tip 28 as is considered highly desirable.

Figure 6:
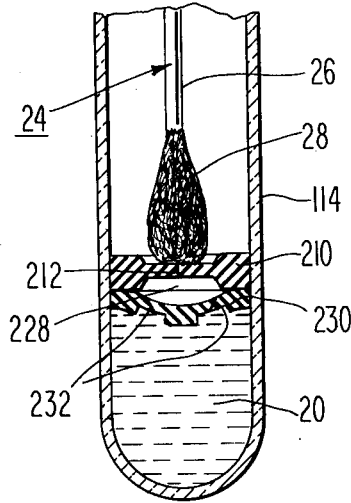
FIG. 6 is a sectional view of a swabbing apparatus representing still another embodiment of the invention.
Figure 6A:
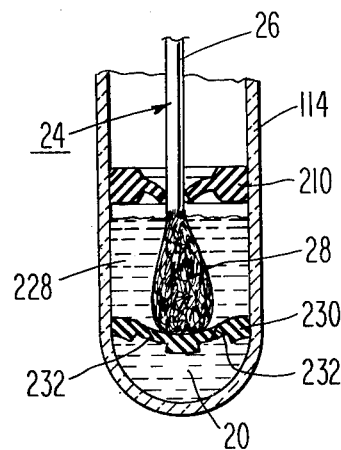
FIG. 6a is a sectional view of the swabbing apparatus of FIG. 6 after the swab has been inserted into the culture-sustaining or transport position.

Another embodiment of the invention is shown in FIG. 6 wherein a barrier member 210 is separable or detached from a plug or piston member 230. As shown in FIG. 6a, insertion of the absorbent tip through an opening 212 to a position which forces the plug member 230 downwardly and forms a chamber 228 which becomes filled with the culture-sustaining liquid 20 which passes through valve 232. The chamber 228 which is formed in part by the barrier member 210 as well as the plug 230 and the sides of the tube 114 is substantially air-tight so as to again permit the taking of anaerobic cultures assuming the use of the proper culture medium 20.

It will be noted that the piston member 230 in FIGS. 6 and 6a tapers inwardly and toward the closed end so as to direct the swab toward the central region of the piston member. In addition, the tapering provides a slightly preformed chamber 228 which allows a substantial portion of the tip 28 to enter the chamber 228 before any culture-sustaining liquid passes through the valves 232 as the plug or piston 230 is advanced toward the closed end of the tube. This in turn minimizes the amount of culture-sustaining liquid which is permitted to pass through the opening 212 before the opening comes in sealing engagement with the elongated member 26 of the swab 24.

Figure 7:
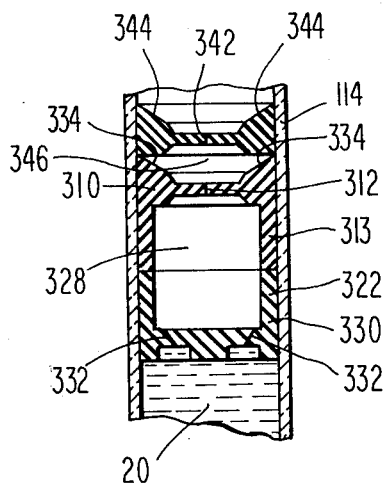
FIG. 7 is a sectional view of a swabbing apparatus representing a further embodiment of the invention.

In the embodiment of FIG. 7, a barrier member 310 is utilized in combination with a separable piston or plug member 330 including axially extending walls 313 and 322 which provide a chamber 328 having an axial length capable of accommodating substantially all of the absorbent tip 28 of the swab 24 shown in FIGS. 5 and 6 before the contact is made between the tip 28 and the bottom of the plug 330. As in the embodiments of FIGS. 5 and 6, the plug portion 310 included a self-sealing opening 312 while the piston member 330 includes valves 332. In addition, the barrier member 310 includes tapered surfaces 334 which taper inwardly and downwardly so as to direct the tip 28 of the swab 24 toward the opening 312.

Another barrier member 340 is shown in FIG. 7 as comprising an opening 342. The barrier member 340 which includes a tapered surface 344 is adapted to form an isolating chamber 346 above the barrier member 310 so as to assure that the culture sustaining liquid is isolated from the open end of the container 114. Such an additional barrier member can be advantageously utilized in the embodiment of FIG. 6 to prevent the culture-sustaining liquid from squirting or traveling up the container 114 when the plug 230 is moved downwardly. Of course, as the swab 24 is forced downwardly, the plug 330 will separate from the barrier member 310 while culture-sustaining liquid is introduced through the valves 332. By providing the rather large chamber 328 before the plug member 330 is moved through the culture-sustaining liquid, a seal at the opening 312 may be formed around the elongated member 26 before the culture-sustaining liquid enters the chamber 328 so as to substantially preclude leakage of the culture-sustaining liquid upwardly beyond the barrier 310.

Figure 8:
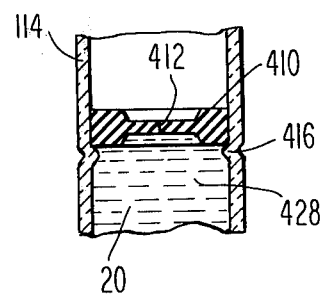
FIG. 8 is a sectional view of a swabbing apparatus representing still a further embodiment of the invention.

The embodiment of FIG. 8 shows a barrier member 410 without any plug portion so as to form a chamber 428 between the barrier member 410 and the closed end of the tube 114. In order to hold the barrier member 410 in place, the tube 114 includes radially inwardly extending projections 416. The barrier member 410 includes an opening 412 which receives the absorbent tip 28 of the swab 24 and forms a seal around the elongated member 26 after passage of the absorbent tip 28 through the opening 412. As in the embodiment of FIGS. 5–7, the cross sectional thickness of the barrier member 410 at the opening 412 is less than the thickness of the barrier 410 adjacent the sides of the tubular member 214.

In the embodiments of FIGS. 5–8, it is particularly important that the seal formed around the openings 112, 212 312 and 412 be substantially fluid tight. This assures that the culture-sustaining liquid will be retained within the chamber below the barrier member. In addition it permits the use of the apparatus in collecting anaerobic cultures by assuring that air cannot enter the chamber within which the absorbent tip 28 is located.

It has been found particularly desirable to utilize an opening which is of a configuration of the elongated member 26. For example, if the elongated member 26 has a cross sectional configuration which is circular, the openings 112, 212, 312 and 412 should be substantially circular. On the other hand, if the cross sectional configuration of the elongated member 26 is rectangular, the openings should be rectangular.

Although specific embodiments of the invention have been shown and described, it will be appreciated that various modifications may be made including the incorporation of features in one embodiment into another embodiment. These modifications and others which will occur to those of ordinary skill in the art fall within the true spirit and scope of the invention as set forth in the appended claims.

What is claimed is:

1. Apparatus for collecting cultures and the like comprising:
   a hollow tubular container having a closed end, an open end and sides extending therebetween;
   a culture-sustaining liquid positioned within the tubular container adjacent the closed end;
   a swab including an elongated member and an absorbent tip; and
   a barrier member extending across said tubular container so as to form a substantially leak-proof barrier between the closed end and the open end, said barrier member including an opening adapted to permit said absorbent tip to pass therethrough into said liquid and form a seal around said elongated member.

2. The apparatus of claim 1 wherein said barrier member comprises an elastic material so to permit said opening to enlarge as said absorbent tip passes therethrough and to contract in sealing engagement with said elongated member after said absorbent tip passes therethrough.

3. The apparatus of claim 2 wherein said barrier member comprises a greater thickness near the sides of said tubular container than near said opening.

4. The apparatus of claim 1 wherein the surface side of said barrier member adjacent said open end of said tubular member tapers inwardly and toward said closed end to guide said absorbent tip toward said opening.

5. The apparatus of claim 1 further comprising a movable piston member extending across said tubular member and in sealing engagement with said sides between said closed end and said barrier member, siad piston member being movable through said culture-sustaining liquid toward said closed end when said swab is inserted through said opening in said barrier member and in pushing contact with said piston member, said piston member including a valve means for allowing said culture-sustaining liquid to enter the area between said barrier and said piston member when said swab is in pushing contact with said piston member.

6. The apparatus of claim 5 wherein said barrier member is attached to said piston member so as to move together through the tubular member when said swab is in pushing contact with said piston member.

7. The apparatus of claim 5 wherein said barrier member is spaced from said piston member a distance at least as great as the axial length of the absorbent tip of said swab.

8. The apparatus of claim 5 wherein said barrier member is detached from said piston member so as to permit said piston member to move through said tubular member independently of movement by said barrier member.

9. The apparatus of claim 8 wherein at least a portion of said barrier member is spaced from said piston member before said swab is in pushing contact with said piston member.

10. The apparatus of claim 5 wherein said piston member tapers inwardly and toward said closed end so as to direct said swab toward the cental region of said piston member.

11. The apparatus of claim 1 including means for restraining the advancement of said barrier member toward said closed end.

12. The apparatus of claim 11 wherein said restraining means comprises an inwardly projecting portion of said tubular container.

13. The apparatus of claim 1 comprising a closure member having an interior surface tapering radially inwardly and downwardly toward said closed end so as to transmit a substantially axial force from said closure member to said barrier member when said closure member contacts the end of said elongated member.

14. The apparatus of claim 1 comprising a closure member having an interior surface tapering radially inwardly and downwardly toward said closed end so as to transmit a substantially axial force from said closure member to said piston member when said closure member contacts the end of said elongated member.

15. Apparatus for collecting cultures and the like, said apparatus comprising:
   a hollow tubular container having a closed end, an open end and sides extending therebetween;

a culture-sustaining liquid positioned within said tubular container adjacent said closed end;

a swab including an elongated member and an absorbent tip;

a movable piston member extending across said tubular member and in sealing engagement with said sides, said piston member being movable through said culture-sustaining liquid toward said closed end when said swab is in pushing contact with said piston member, said piston member including a valve means for allowing said culture-sustaining liquid to enter the area between said open end and said piston member when said swab is in pushing contact with said piston member; and means associated with said piston member for forming a sealed chamber capable of enclosing at least a portion of said swab including said tip, said chamber adapted to contain culture-sustaining liquid which has passed through said valve means.

16. The apparatus of claim 15 wherein said chamber forming means includes an opening adapted to permit said absorbent tip to pass therethrough into said liquid and form a seal around said elongated member.

17. The apparatus of claim 16 wherein said chamber forming means comprises a barrier member attached to said piston member.

18. The apparatus of claim 17 wherein said barrier member comprises a first separate piece and said piston member comprises a second separate piece, said first separate piece being physically attached to said second separate piece.

19. The apparatus of claim 16 wherein said chamber forming means comprises a barrier member detached from said piston member so as to permit said piston member to move through said tubular member independently of any movement of said barrier member.

20. The apparatus of claim 19 wherein said piston member tapers inwardly and downwardly toward said closed end so as to direct said swab toward the central region of said piston member.

21. An improved method of collecting cultures in a live condition utilizing an apparatus comprising a collection tube having sides and a bottom, a culture-sustaining liquid adjacent the bottom of said tube, a swab including an elongated member having an absorbent tip, and barrier means extending across said tube above said liquid, said barrier means having a self-closing opening therein, the improved method comprising the steps of:

swabbing an area of culturable material with the absorbent swabbing tip of the swab;

inserting the swab into the tube;

forcing the absorbent tip of the swab through the self-closing opening of the barrier means so as to permit the liquid to saturate the tip; and forming a seal at said self-closing opening around said elongated member so as to substantially prevent the passage of air through said barrier means to said absorbent tip.

22. The improved method of claim 21 wherein said apparatus comprises a plug located within the tube above the liquid and below the barrier means, said plug sealingly engaging the sides of said tube and having an isolating valve remaining closed when the plug is stationary above the liquid and open when the plug is moved downwardly through the liquid, the method further comprising the steps of:

transmitting a downward force to the plug through the swab after the absorbent tip has passed through the opening in said barrier means;

introducing culture-sustaining liquid into saturating contact with the absorbent tip as a function of the swab position; and closing the valve when the swab comes to rest in the tube so as to substantially isolate any culture-sustaining liquid remaining adjacent the bottom of the tube from the swab.

* * * * *

UNITED STATES PATENT OFFICE
CERTIFICATE OF CORRECTION

Patent No. 4,014,746      Dated March 29, 1977

Inventor(s) Donald J. Greenspan

It is certified that error appears in the above-identified patent and that said Letters Patent are hereby corrected as shown below:

Column 1, line 7, change "issued" to read --issue--.

Column 1, line 34, change "in" to read --is--.

Column 4, line 26, change "that" to read --than--.

Column 8, line 17, change "siad" to read --said--.

Column 8, line 45, change "cental" to read --central--.

Signed and Sealed this

Fourteenth Day of June 1977

[SEAL]

Attest:

RUTH C. MASON
*Attesting Officer*

C. MARSHALL DANN
*Commissioner of Patents and Trademarks*